(12) United States Patent
Inan et al.

(10) Patent No.: US 9,215,991 B2
(45) Date of Patent: *Dec. 22, 2015

(54) SYSTEMS AND METHODS FOR MONITORING HEART FUNCTION

(71) Applicant: The Board of Trustees of the Leland Stanford Junior University, Palo Alto, CA (US)

(72) Inventors: Omer T. Inan, Palo Alto, CA (US); Mozziyar Etemadi, San Francisco, CA (US); Laurent B. Giovangrandi, Palo Alto, CA (US); Gregory T. Kovacs, Palo Alto, CA (US); Richard M. Wiard, Campbell, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/726,069

(22) Filed: May 29, 2015

(65) Prior Publication Data

US 2015/0257680 A1    Sep. 17, 2015

Related U.S. Application Data

(63) Continuation of application No. 14/498,593, filed on Sep. 26, 2014, now Pat. No. 9,055,871, which is a continuation of application No. 12/579,264, filed on Oct. 14, 2009, now Pat. No. 8,870,780.

(60) Provisional application No. 61/105,696, filed on Oct. 15, 2008.

(51) Int. Cl.
| | |
|---|---|
| *A61B 5/026* | (2006.01) |
| *A61B 5/11* | (2006.01) |
| *A61B 5/0205* | (2006.01) |
| *G01G 19/50* | (2006.01) |
| *A61B 5/00* | (2006.01) |
| *A61B 5/0456* | (2006.01) |

(Continued)

(52) U.S. Cl.
CPC ............. *A61B 5/1102* (2013.01); *A61B 5/0006* (2013.01); *A61B 5/0024* (2013.01);
(Continued)

(58) Field of Classification Search
CPC .... A61B 5/1102; A61B 5/0205; A61B 5/721; G01G 19/50
USPC .................................. 600/481, 508, 526, 527
See application file for complete search history.

(56) References Cited

U.S. PATENT DOCUMENTS

| | | | |
|---|---|---|---|
| 3,702,113 A | 11/1972 | Blockley | |
| 4,195,643 A | 4/1980 | Pratt, Jr. | |

(Continued)

FOREIGN PATENT DOCUMENTS

| | | | |
|---|---|---|---|
| ES | 2296474 B1 | 4/2008 | |
| ES | 2328205 B1 | 10/2009 | |

(Continued)

OTHER PUBLICATIONS

H. Mandelbaum and R.A. Mandelbaum, "Studies Utilizing the Portable Electromagnetic Ballistocardiograph: IV. The Clinical Significance of Serial Ballistocardiograms Following Acute Myocardial Infarction," Circulation, vol. 7, pp. 910-9165 (1953).

(Continued)

*Primary Examiner* — Theodore Stigell
*Assistant Examiner* — Michael Carey
(74) *Attorney, Agent, or Firm* — Crawford Maunu PLLC (57) ABSTRACT

Characteristics of a user's heart are detected. In accordance with an example embodiment, a ballistocardiogram (BCG) sensor is used to detect heart characteristics of a user, and provide a BCG output indicative of the detected heart characteristics. The BCG output is further processed using data from one or more additional sensors, such as to reduce noise and/or otherwise process the BCG signal to characterize the user's heart function.

20 Claims, 5 Drawing Sheets

(51) Int. Cl.
*A61B 5/04* (2006.01)
*A61B 5/029* (2006.01)
*A61B 5/024* (2006.01)

(52) U.S. Cl.
CPC .............. *A61B5/0205* (2013.01); *A61B 5/029* (2013.01); *A61B 5/04017* (2013.01); *A61B 5/0456* (2013.01); *A61B 5/486* (2013.01); *A61B 5/4836* (2013.01); *A61B 5/721* (2013.01); *G01G 19/50* (2013.01); *A61B 5/02416* (2013.01)

(56) References Cited

U.S. PATENT DOCUMENTS

| | | | |
|---|---|---|---|
| 4,362,164 | A | 12/1982 | Little et al. |
| 4,557,271 | A | 12/1985 | Stoller et al. |
| 4,657,025 | A | 4/1987 | Orlando |
| 4,679,569 | A | 7/1987 | Lee |
| 4,765,321 | A | 8/1988 | Mohri |
| 4,836,215 | A | 6/1989 | Lee |
| 4,947,857 | A | 8/1990 | Albert et al. |
| 4,958,638 | A | 9/1990 | Sharpe et al. |
| 5,431,170 | A | 7/1995 | Mathews |
| 5,620,003 | A | 4/1997 | Sepponen |
| 5,682,902 | A | 11/1997 | Herleikson |
| 6,228,033 | B1 | 5/2001 | Koobi et al. |
| 6,331,162 | B1 | 12/2001 | Mitchell |
| 6,454,719 | B1 | 9/2002 | Greenhut |
| 6,702,754 | B2 | 3/2004 | Ogura et al. |
| 6,783,498 | B2 | 8/2004 | Sackner et al. |
| 6,814,705 | B2 | 11/2004 | Kawaguchi et al. |
| 7,137,955 | B2 | 11/2006 | Bartels et al. |
| 7,313,435 | B2 | 12/2007 | Nakada et al. |
| 7,417,536 | B2 | 8/2008 | Lakshmanan et al. |
| 7,787,946 | B2 | 8/2010 | Stahmann et al. |
| 7,846,104 | B2 * | 12/2010 | MacQuarrie et al. ......... 600/481 |
| 7,899,522 | B1 | 3/2011 | Koh et al. |
| 8,452,390 | B2 | 5/2013 | Jensen |
| 8,473,041 | B2 | 6/2013 | Bartnik et al. |
| 8,548,556 | B2 | 10/2013 | Jensen |
| 8,682,424 | B2 | 3/2014 | Tsoglin et al. |
| 8,870,780 | B2 * | 10/2014 | Inan et al. ................. 600/481 |
| 9,055,871 | B2 * | 6/2015 | Inan et al. .......................... 1/1 |
| 2002/0188205 | A1 | 12/2002 | Mills |
| 2003/0233034 | A1 | 12/2003 | Varri et al. |
| 2004/0073127 | A1 | 4/2004 | Istvan et al. |
| 2004/0097802 | A1 | 5/2004 | Cohen |
| 2004/0249258 | A1 | 12/2004 | Tupin, Jr. et al. |
| 2005/0004483 | A1 | 1/2005 | Lin |
| 2005/0043645 | A1 | 2/2005 | Ono et al. |
| 2005/0119711 | A1 | 6/2005 | Cho et al. |
| 2005/0171451 | A1 | 8/2005 | Yeo et al. |
| 2006/0111641 | A1 | 5/2006 | Loren et al. |
| 2006/0116589 | A1 | 6/2006 | Park |
| 2006/0149139 | A1 | 7/2006 | Bonmassar et al. |
| 2007/0293770 | A1 | 12/2007 | Bour et al. |
| 2008/0161700 | A1 | 7/2008 | Sachanandani et al. |
| 2008/0194975 | A1 | 8/2008 | MacQuarrie et al. |
| 2008/0306393 | A1 | 12/2008 | Ting et al. |
| 2009/0024044 | A1 | 1/2009 | Virtanen et al. |
| 2009/0182204 | A1 | 7/2009 | Semler et al. |
| 2009/0203972 | A1 | 8/2009 | Heneghan et al. |
| 2010/0016685 | A1 | 1/2010 | Muehlsteff et al. |
| 2010/0094147 | A1 | 4/2010 | Inan et al. |
| 2010/0210921 | A1 | 8/2010 | Park et al. |

FOREIGN PATENT DOCUMENTS

| | | |
|---|---|---|
| ES | 2385898 A1 | 2/2012 |
| ES | 2398439 A2 | 3/2013 |
| ES | 2398542 A2 | 3/2013 |
| GB | 2367896 A | 4/2002 |
| JP | 2007283071 A | 11/2007 |
| JP | 2009050508 A | 3/2009 |
| KR | P0137272 | 2/1998 |
| KR | 10-2005-0079235 | 8/2005 |
| WO | 2005074379 A2 | 8/2005 |
| WO | 2006088280 A1 | 8/2006 |
| WO | 2008102298 | 8/2008 |
| WO | 2010/004502 | 1/2010 |
| WO | 2010045455 A1 | 4/2010 |
| WO | 2011075767 A1 | 6/2011 |

OTHER PUBLICATIONS

R.S. Guber, M. Rodstein and H.E. Ungerleider, "Ballistocardiograph: An Appraisal of Technic, Physiological Principles, and Clinic Value," Circulation, vol. 7, pp. 268-286 (1953).
M.B. Rappaport, H.B. Sprague, and W.B. Thompson, "Ballistocardiography: I. Physical Considerations," Circulation, vol. 7, pp. 229-246 (1953).
O. Tannenbaum, J. Schack and H. Vesell, "Relationship between Ballistocardiographic Forces and Certain Events in the Cardiac Cycle," Circulation, vol. 6, pp. 586-592 (1952).
T.E. Satterthwaite, "Cardiovascular Diseases: Recent Advances in Their Anatomy, Physiology, Pathology, Diagnosis and Treatment," Lemcke and Beuschner, New York, NY (1913).
J.W. Gordon, "On Certain Molar Movements of the Human Body Produced by the Circulation of the Blood," J. of Anat. Anat. Phys., vol. 11, pp. 533-536 (1877).
Inan O. T. et al., "Novel methods for estimating the ballistocardiogram signal using a simultaneously acquired electrocardiogram", Proceedings of the 31st Annual International Conference of the IEEE Engineering in Medicine and Biology Society: Engineering the Future of Biomedicine, EMBC 2009, IEEE, (Sep. 3, 2009), pp. 5334-5347.
Websters Ninth New Collegiate Dictionary. Meriam Webster Inc., 1990, p. 1152.
Fang, A. et al. "Using a Geophone for Vibration Cancellation in a STM." Bulletin of the American Physical Society, 2008 APS March Meeting, vol. 53, No. 3, Mar. 10, 2008 (Abstract only).
de Viries, S.O. et al. "Prediction of the Left Ventricular Mass from the Electrogram in Systemic Hypertension." American Journal of Cardiology, May 1, 1996; 11:974-8 (Abstract only).
HeartForce Medical Inc. "Definitions and Terminologies; History of Seismocardiology." www.heartforcemedical.com, printed Aug. 20, 2013, 4 pgs.
J. Alametsä et al. "Ballistocardiogaphic studies with acceleration and electromechanical film sensors." Medical Engineering & Physics 31 (2009), p. 1154-1165.
J. Alametsä et al. "Arterial Elasticity Measurements with Ankle Pulse Width Velocity and Ballistocardiography." ECIFMBE 2008, IFMBE Proceedings 22, p. 1636-1641.
J. Allen. "Photoplethysmography and its application in clinical physiological measurement." Physiol. Meas. 28, 2007, p. R1-R39.
A. Avolio et al. "Role of Pulse Pressure Amplification I Arterial Hpertension: Experts' Opinion and Review of the Data." Hypertension, vol. 54, Aug. 1, 2009, p. 375-383.
J. Blacher et al. "Aortic Pulse Wave Velocity as a Marker of Cardiovascular Risk in Hypertensive Patients," Hypertension, vol. 33, 1999, p. 1111-1117.
Davis, S; B. van den Bogaard et al. "Active standing reduces wave reflection in the presence of increased peripheral resistance in young and old healthy individuals." J Hypertension (4) Apr. 29, 2011, p. 682-689 (Abstract); and B. van den Bogaard. "Chapter 12: Active standing reduces wave reflection in the presence of increased peripheral resistance in young and old healthy individuals." Dissertation, Univ. Amsterdam, 2012, p. 180-193.
G. Kim et al. "Vascular Variation of PTT and the Vascular Characteristic Index According to the Posture Change." In Proceedings of the 2007 International Conference on Convergence Information Technology (ICCIT '07). IEEE Computer Society, Nov. 2007, p. 2426-2425. Abstract Only.
E. Pinheiro et al. "Non-Intrusive Device for Real-Time Circulatory System Assessment with Advanced Signal Processing Capabilities." Measurement Science Review, vol. 10, No. 5, 2010, p. 167-175.

(56) References Cited

OTHER PUBLICATIONS

E. Pinheiro et al. "Pulse arrival time and ballistocardiogram application to blood pressure variability estimation." Medical Measurements and Applications, 2009. IEEE Workshop, May 29-30, 2009. Abstract only.

R. Wiard et al. "Estimation of Central Aortic Forces in the Ballistocardiogram under Rest and Exercise Conditions." 31st Annual International Conference of the IEEE EMBS, Sep. 2-6, 2009, p. 2831-2834.

R. Wiard et al. "Automatic detection of motion artifacts in the ballistocardiogram measured on a modified bathroom scale." Med Biol Eng Comput (2011) 49:213-220. Published online Dec. 9, 2010

B. Williams et al. "Differential Impact of Blood Pressure-Lowering Drugs on Central Aortic Pressure and Clinical Outcomes: Principal Results of the Conduit Artery Function Evaluation (CAFE) Study," Circulation, vol. 113, Feb. 13, 2006, p. 1213-1225.

Inan, OT, Etemadi M, Paloma A, Giovangrandi L, Kovacs GTA (2009) Non-invasive cardiac output trending during exercise recovery on a bathroom-scale-based ballistocardiograph. Physiol Meas 30:261-274 Abstract / Introduction Only.

Inan, OT, Kovacs GTA, Giovangrandi L (2010) Evaluating the lower-body electromyogram signal acquired from the feet as a noise reference for standing ballistocardiogram measurements. IEEE Trans Inf Technol Biomed 14:1188-1196 Abstract / Introduction Only.

DeLoach SS, Twonsend RR, "Vascular Stiffness: Its Measurement and Significance for Epidemiologic and Outcome Studies", Clin J Am Soc Nephrol, 3: 184-192, 2008. Abstract / Introduction Only.

Gonzalez, et al. "Deteccion de las frecuencias 1-9 cardiaca and respitatoria mediante una bascu the electronica" In: IFMBE Proceedings. vol. 18, pp. 448-451, 2007. Springer-Verlag Berlin Heidelberg.

Gomez-Clapers J. et al. "Pulse arrival time estimation from the impedance plethysmogram obtained with a handheld device", 33rd Annual International Conference of the IEEE EMBS, Boston, USA, Mar. 8-9, 2011, pp. 516-519. Abstract only.

A Akhbardeh, M Koivuluoma, T Koivistoinen, A Värri, Ballistocardiogram diagnosis using neural networks and shift-invariant daubechies wavelet transform. Proceedings of 13th European Signal Processing Conference (EUSIPCO '05), Sep. 2005, Antalya, Turkey, 4.

O. Inan, M. Etemadi, R. Wiard, L. Giovangrandi, and G. Kovacs, "Evaluating the Foot Electromyogram Signal as a Noise Reference for a Bathroom Scale Ballistocardiogram Recorder," Computer-Based Medical Systems, 2008. CBMS '08. 21st IEEE International Symposium on , vol., no., pp. 70,74, Jun. 17-19, 2008.

O. Inan and G. Kovacs, "An 11 µW, Two-Electrode Transimpedance Biosignal Amplifier with Active Current Feedback Stabilization," IEEE Transactions on Biomedical Circuits and Systems (2009).

O. Inan, M. Etemadi, B. Widrow and G. T. A. Kovacs, "Adaptive cancellation of floor vibrations in standing ballistocardiogram measurements using a seismic sensor as a noise reference," IEEE (2009).

O.T. Inan M. Etemadi, R. M. Wiard, L. Giovangrandi, and G. T. A. Kovacs, "Robust Ballistocardiogram Acquisition for Home Monitoring," Phys. Meas., vol. 30, No. 2, pp. 169-185 (2009).

R. F. Yazicioglu, P. Merken, R. Puers and C. Van Hoof, "A 60 µW 60 nV/√Hz Readout Front-End for Portable Biopotential Acquisition Systems," IEEE Journ. of Solid-State Circuits, vol. 42, No. 5 (May 2007).

W. Rosamond et al., "Heart Disease and Stroke Statistics—2007 Update: A Report from the American Heart Association Statistics Committee and Stroke Statistics Subcommittee," Circ., vol. 115, pp. 69-171 (2007).

R. R. Harrison, "A Versatile Integrated Circuit for the Acquisition of Biopotentials," IEEE CICO, pp. 115-122 (2007).

T. Denison, K. Consoer, W. Santa, A.-T. Avestruz, J. Cooley, and A. Kelly, "A 2µW 100 nV/rtHz, Chopper-Stabilized Instrumentation Amplifier for Chronic Measurement of Neural Field Potentials," IEEE Jour. Solid-State Circuits, vol. 42, No. 12, pp. 2934-2945 (2007).

A.Akhbardeh, S. Junnila, M. Koivuluoma, T. Koivistoinen, V. Turjanmaa, T. Kööbi, and A. Värri, "Towards a heart disease diagnosing system based on force sensitive chair's measurement, biorthogonal wavelets and neural networks," ScienceDirect, Engineering Applications for Artificial Intelligence, pp. 1-10 (2006).

D. Corrado, C. Basso, A. Pavel, P. Michieli, M. Schiavon, and G. Thiene, "Trends in Sudden Cardiovascular Death in Young Competitive Athletes After Implementation of a Preparticipation Screening Program," JAMA, vol. 296, No. 13, pp. 1593-1601 (Oct. 4, 2006).

C.N. Chien and F.S. Jaw, "Miniature ultra-low-power biopotential amplifier for potable [sic] applications," Biomedical Engineering-Applications, Basis & Communications, vol. 17, No. 2, pp. 11-49 (Apr. 2005).

C.W. Mundt, K.N. Montgomery, U.E. Udoh, V.N. Barker, G.C. Thonier, A.M. Tellier, R.D. Ricks, R.B. Darling, Y.D. Cagle, N.A. Cabrol, S.J. Ruoss, J.L. Swain, J.W. Hines, and G.T.A. Kovacs, "A Multiparameter Wearable Physiologic Monitoring System for Space and Terrestrial Applications," IEEE Trans. Inform. Tech. In Biomed., vol. 9, No. 3, pp. 382-391 (Sep. 2005).

M. Shojaei-Baghini, R.K. Lal, and D.K. Sharma, "A Low-Power and Compact Analog CMOS Processing Chip for Portable ECG Recorders," Proc. IEEE A.S.S.C.C., pp. 473-476 (2005).

J. Alametsa, A. Värri, M. Koivuluoma, and L. Barna, "The Potential of EMFi Sensors in Heart Activity Monitoring," 2nd OpenECG Workshop "Integration of the ECG into the EHR & Interoperability of ECG Device Systems," Apr. 1-3, 2004 Berlin, Germany.

E. Company-Bosch and E. Hartmann, "ECG Front-End Design is Simplified with MicroConverter," Analog Dialogue, 37-11, pp. 1-5 (Nov. 2003).

D.M. Linton and D. Gilon, "Advances in noninvasive cardiac output monitoring," Annals of Cardiac Anaesthesia, vol. 5, pp. 141-148 (2002).

M. Watanabe, J. Marine, R. Sheldon, and M. Josephson, "Effects of Ventricular Premature Stimulus Coupling Interval on Blood Pressure and Heart Rate Turbulence," Circ., vol. 106, pp. 325-330 (2002).

K. Lu, J. W. Clark, Jr. F. H. Ghorbel, D. L. Ware, and A. Bidani, "A human cardiopulmonary system model applied to the analysis of the Valsalva maneuver," Am. J Physiol. Heart Circ. Physiol., vol. 281, pp. H2661-H2679 (2001).

J. Rapoport, D. Teres, J. Steingrub, T. Higgins, W. McGee, and S. Lemeshow, "Patient characteristics and ICU organizational factors that influence frequency of pulmonary artery catheterization," JAMA, vol. 283, No. 19, pp. 2559-2567 (2000).

B.D. Johnson, K.C. Beck, D.N. Proctor, J. Miller, N.M. Dietz, and M.J. Joyner, "Cardiac output during exercise by the open circuit acetylene washin method: comparison with direct Fick," J. Appl Physiol, vol. 88, pp. 1650-1658 (2000).

W. Klimesch, "EEG alpha and theta oscillations reflect cognitive and memory performance: a review and analysis," Brain Research Reviews, vol. 29, pp. 169-195 (1999).

D. Corrado, C. Basso, M. Schiavon, and G. Thiene, "Screening for Hypertrophic Cardiomyopathy in Young Athletes," NEJM, vol. 339, pp. 364-369 (Aug. 6, 1998).

A.C. MettingVanRijn, A. Peper and C.A. Grimbergen, "Amplifiers for bioelectric events: a design with a minimal number of parts," Med. & Biol. Eng. & Comput, vol. 32, pp. 305-310 (1994).

R. Moore, R. Sansores, V. Guimond, and R. Abboud, "Evaluation of cardiac output by thoracic electrical bioimpedance during exercise in normal subjects," American College of Chest Physicans, vol. 102, pp. 448-455 (1992).

J. Christie, L.M. Sheldahl, F.E. Tristani, K.B. Sagar, M.J. Ptacin, and S. Wann, "Determination of stroke volume and cardiac output during exercise: comparison of two-dimensional and Doppler echocardiography, Fick oximetry, and thermodilution," Circ., vol. 76, pp. 539-547 (1987).

H. Benjelloun, R. Itti, L. Philippe, J.M. Lorgeron and M. Brochier, "Beat-to-Beat Assessment of Left Ventricular Ejection in Atrial Fibrillation," European Journal Nuclear Medicine, vol. 8, pp. 206-210 (1983).

S. Grimnes, "Impedance measurement of individual skin surface electrodes," Med. & Biol. Eng. & Comput., vol. 21, pp. 750-755 (1983).

(56) References Cited

OTHER PUBLICATIONS

Y. Miyamoto, M. Takahashi, T. Tamura, T. Nakamura, T. Hiura, and M. Mikami, "Continuous determination of cardiac output during exercise by the use of impedance plethysmogrphy," Med. Biol. Eng. Comp., vol. 19, pp. 638-644, (1981).

R.P. Lewis, S.E. Rittogers, W.F. Froester, and H. Boudoulas, "A critical review of the systolic time intervals," Circulation, vol. 56, pp. 146-158 (1977).

I. Starr and F.C. Wood, "Twenty-Year Studies with the Ballistocardiograph: The Relation Between the Amplitude of the First Record of 'Healthy' Adults and Eventual Mortality and Morbidity from Heart Disease," Circulation, vol. 36, pp. 714-732 (1961).

D.C. Deuchar, S.A. Talbot, and W.R. Scarborough, "Some Observations on the Relation of the High-Frequency Bed Ballistocardiogram to that Obtained from an Aperiodic Bed," Circulation, vol. 11, pp. 228-239 (1955).

\* cited by examiner

SYSTEMS AND METHODS FOR MONITORING HEART FUNCTION

RELATED PATENT DOCUMENTS

This patent document is a continuation under 35 U.S.C. §120 of U.S. patent application Ser. No. 14/498,593 filed on Sep. 26, 2014 (U.S. Pat. No. 9,055,871) and which included Appendices A-G, which is further a continuation of U.S. patent application Ser. No. 12/579,264 filed on Oct. 14, 2009 (U.S. Pat. No. 8,870,780), which claims the benefit 35 U.S.C. §119(e) of U.S. Provisional Patent Application Ser. No. 61/105,696 filed on Oct. 15, 2008, which included five appendices (A through E) that provide example and experimental results for use with various embodiments of the present invention, and which further cite various references, each of these patent documents are fully incorporated herein by reference.

FIELD OF INVENTION

This invention relates generally to monitoring of heart function, and in specific instances to systems and methods for detecting heart function and processing signals therefor.

BACKGROUND

The National Institutes of Health (NIH) estimate that over 500,000 annual hospital admissions for heart failure patients are avoidable. Heart failure is a tremendous problem in the United States that affects millions of people and costs billions of health care dollars each year. A number of tests allow a doctor to assess heart function; however, proper implementation of many of these tests requires expensive equipment and/or a qualified professional. This makes it difficult and expensive to monitor the condition of a patient, as the patient must routinely visit the hospital or risk late detection of a worsening heart condition.

These troubling numbers have led researchers and companies to improve the methods for monitoring heart failure outpatients with the goal of reducing unnecessary hospital readmissions and costs. One proposed solution transmits a patient's body weight measured on a bathroom scale to his/her physician because increasing body weight could be a sign of fluid retention, which might result from a worsening heart condition. Such diagnostic mechanisms are, however, less than ideal. Body weight can be affected by factors other than fluid retention, and fluid retention can be caused by factors other than heart conditions. Thus, such techniques result in false positives, or worse, fail to detect worsening heart conditions.

The ballistocardiogram (BCG) is a non-invasive diagnostic technique which measures the mechanical recoil of the body in reaction to the ejection of blood from the heart through the vasculature. BCG measurement methods were developed in the mid-1900s and largely abandoned in the early 1960s due to impracticality and unreliability. Reliable and practical BCG signal acquisition would provide an excellent tool for evaluating a patient's cardiovascular health. However, such signal acquisition remains challenging for use in a variety of applications.

SUMMARY

The present invention is directed to approaches to systems and methods for monitoring of heart function. The present invention is exemplified in a number of implementations and applications including those presented below, which are commensurate with certain claims included with this patent document.

According to an example embodiment, a system provides BCG (ballistocardiogram) data from a user. The system includes a BCG capture device, a secondary sensor and a processor circuit. The BCG capture device includes a heart-characteristic sensor that captures, from the user, a BCG signal indicative of at least one of physical movement and mechanical output of the user's heart. The secondary sensor detects an indication of at least one of noise present in the BCG signal and a physiologic characteristic of the user, and provides an output characterizing the detected indication. The processor circuit uses the secondary sensor output to process the captured BCG signal and to generate an output BCG signal indicative of a condition of the user's heart. For example, the BCG signal may be processed via filtering or another type of modification that uses the secondary sensor's detection as an input to alter the signal.

Consistent with another example embodiment of the present invention, a system/method provides ballistocardiogram (BCG) measurements (e.g., in real-time) from a user standing on a BCG capture device. A force sensor is arranged to capture a signal indicative of the physical movement and/or mechanical output of the heart of the user while the user is standing on the device. A second specific sensor type (e.g., ECG, accelerometer, geophone, displacement, electromyogram or video imaging device) provides additional information about the captured signal, which may be indicative of noise and/or interference present in the BCG measurement, or of other characteristics of the user. A processor uses the second-sensor signal to process the captured signal, such as to filter or gate (e.g., weight or eliminate aspects of) a captured BCG recording, and provide user diagnostics.

In some implementations, a captured BCG recording is gated to weight or eliminate segments of the recording that contain higher than usable noise or interference levels (e.g., for averaging algorithms). For example, regions of higher noise can be given proportionally lower weighting in weighted ensemble averaging algorithms, such as maximum likelihood averaging.

Another example embodiment is directed to a system for providing BCG (ballistocardiogram) data from a user. The system includes a BCG capture device, a secondary sensor and a processor circuit. The BCG capture device includes a heart-characteristic sensor that captures, from the user, a BCG signal indicative of at least one of physical movement and mechanical output of the user's heart. The secondary sensor detects an indication of at least one of noise present in the BCG signal and a physiologic characteristic of the user (e.g., a heart characteristic and/or a noise-based characteristic), and provides an output characterizing the detected indication. The processor circuit uses the secondary sensor output to process the captured BCG signal and generate an output BCG signal indicative of a condition of the user's heart.

The above summary of the present invention is not intended to describe each illustrated embodiment or every implementation of the present invention.

BRIEF DESCRIPTION OF THE FIGURES

The invention may be more completely understood in consideration of the detailed description of various embodiments of the invention that follows in connection with the accompanying drawings, in which.

While the invention is amenable to various modifications and alternative forms, examples thereof have been shown by way of example in the drawings and will be described in detail. It should be understood, however, that the intention is not to limit the invention to the particular embodiments shown and/or described. On the contrary, the intention is to cover all modifications, equivalents, and alternatives falling within the spirit and scope of the invention.

DETAILED DESCRIPTION

Various embodiments of the present invention have been found to be particularly useful in connection with monitoring heart function (e.g., to determine cardiac health of a patient) in a manner that facilitates home use by the patient. While the present invention is not necessarily limited to such applications, various aspects of the invention may be appreciated through a discussion of various examples using this context.

Aspects of the present invention are directed to detecting the heart function of a user with a sensor that detects weight and/or weight variances of a user. A processing arrangement is configured (e.g., with an algorithm/transform) to determine heart function characteristics of the user based upon the detected weight and/or weight variances. The processing arrangement uses data from one or more additional sensors as a parameter of the algorithm/transform. In connection with these example aspects, it has been discovered that such implementations can be particularly useful for producing unexpectedly practical and reliable BCG measurements.

In another example embodiment, a BCG (ballistocardiogram) system includes a BCG capture device including a heart-characteristic sensor that captures, from a user, a BCG signal indicative of at least one of physical movement and mechanical output of the user's heart. A secondary sensor detects a secondary characteristic relating to the BCG signal, and provides an output characterizing the detected indication. For example, the secondary sensor may detect characteristics of a user and/or of the user's environment to provide an indication of one or more of noise present in the BCG signal and a physiologic characteristic of the user. A processor circuit uses the secondary sensor output to process the captured BCG signal and to generate an output BCG signal indicative of a condition of the user's heart.

In some implementations, the BCG capture device includes a weighing scale, and the secondary sensor includes an electrocardiogram (ECG) sensor that detects an ECG signal from the user, or a photoplethysmograph sensor that detects blood flow pulsations of the user. This detected signal is used to process a signal obtained via the BCG capture device.

In another implementation, the secondary sensor includes an ECG sensor that detects an ECG signal from the user that is indicative of, or otherwise useful for determining, characteristics of the user and related BCG signal capture. The processor circuit uses an algorithm to process the captured BCG signal and to generate the output BCG signal using the detected ECG signal as an input to the algorithm to process the BCG signal. In certain applications, the processor circuit generates an output BCG signal based upon an ensemble-average of the detected BCG signal generated via the detected ECG signal. This averaging can be both static—providing a single ensemble-averaged BCG beat—or dynamic, as in synchronous moving averaging or exponentially-weighted triggered averaging.

In some implementations, data is detected for both BCG- and ECG-based analysis using a strip-type sensor or a handlebar-type sensor that may be implemented on a scale device as discussed herein (see, e.g., FIG. 1A and FIG. 1B, discussed further below). One or more such sensors are used to effectively capture a signal from a user that is subsequently processed to generate both BCG and ECG analysis data. In some implementations, ECG data that is detected and/or generated is used in the generation of BCG analysis data, such as by filtering a captured signal to facilitate the representation of one or more of physical movement and mechanical output of the user's heart. For example, BCG and ECG (or photoplethysmograph) signals can be adaptively filtered, or processed via ECG R-wave (or photoplethysmograph peak) triggered ensemble averaging or triggered moving averaging, to improve the signal-to-noise ratio and the consistency of BCG recordings.

In some embodiments, a strip-type or handlebar-type sensor as discussed above includes a two-electrode ECG circuit configured for contacting the hands of a user. In some implementations, the two-electrode ECG circuit uses active current feedback to one electrode to reduce amplifier saturation problems, rendering higher signal quality on the ECG recordings. Detected ECG characteristics can then be used for adaptively filtering, ensemble averaging, or otherwise processing the BCG signal measured from the force sensor in the scale, to improve the signal quality of the BCG.

In some implementations, the ECG or photoplethysmograph (or other reference signal) is adaptively filtered to estimate the BCG to mitigate requirements or needs for detecting peaks or heartbeat segmentation, or use of an R-wave detector (e.g., for ensemble averaging or triggered moving averaging). In some implementations, an ECG or photoplethysmograph signal is input directly into an adaptive filter, with the raw BCG signal as the desired response; the output of this filter, to form a best least-squares estimate of the signal without any need for ECG or photoplethysmograph peak detection. In some implementations, a least-mean squares algorithm is used to adapt weights of the adaptive filter. The convergence rate can be chosen to be slow, allowing the filter to converge to the best solution for the user of the device.

Another embodiment is directed to a BCG capture device as discussed above, including a weighing scale that includes the heart-characteristic sensor. The processor circuit processes the captured BCG signal, using previously-obtained data including cardiac output and stroke volume data for the user (e.g., derived from Doppler ultrasound measurements) and both RMS power and an ensemble-average amplitude of the BCG signal, to generate an estimated output BCG signal indicative of the cardiac output and stroke volume of the user's heart. In some implementations, the processor circuit receives the previously-obtained cardiac data from a remote location. In other implementations, the processor compares the captured BCG signal to a baseline value, which is based upon cardiac output and stroke volume data for the user and both RMS power and an ensemble-average amplitude of the BCG signal, to generate an output BCG signal indicative of the cardiac output and stroke volume of the user.

A specific implementation involves the use of a scale having custom electronic circuitry for acquiring and processing the BCG signal. Users of the scale position themselves on the scale. The weight is measured and recorded as a function of time. The sensitivity of the measurement is sufficient in both weight and sample speed so that the generated/recorded signal contains the desired BCG signal. For relatively small BCG signals (compared to a number of other sources of force variances such as respiration, user movement, building vibrations and/or electrical noise), aspects of the present invention are directed to detecting the BCG signal, relative to one or more of the aforesaid sources. In some implementations, the amplitude of the BCG signal is corrected based upon the weight of a user, based on kinetic energy transfer. A variety of scales, customized or otherwise coupled for acquiring a BCG signal, can be implemented in connection with various example embodiments. For instance, the Omron HBF-500 Body Composition Monitor/Scale available from Omron Healthcare Inc., of Bannockburn, Ill. can be implemented in connection with one or more example embodiments.

In another example embodiment, a BCG characteristic is detected in connection with the detection of characteristics in an implantable pacemaker or cardioverter defibrillator (ICD), and can further be used in connection with the characteristics of the pacemaker or ICD for analysis and/or correction. For instance, the detected BCG characteristic can indicate the responsiveness of the cardiovascular system to various settings within the pacemaker, and can be used for improving the responsiveness or coordination of heart contractions by varying the parameters of the implantable device. In some implementations, the baseline heart rate setting of a pacemaker can be increased or decreased based on changes over time in a person's BCG characteristic, such as a decreasing trend in BCG RMS power over several days or weeks. In some implementations, the pacing pulse timings of the pacemaker can be used for triggered averaging, moving averaging, or adaptively filtering the BCG signal of the user. Since the timing of these pacing pulses is deterministically known by the processor, the averaging or filtering algorithms will be more accurate than, for example, if the R-wave peak of the ECG characteristic was used for averaging or filtering.

In another example embodiment, a BCG characteristic is detected in connection with the detection of characteristics for pacemaker adjustment, such as in cardiac resynchronization therapy (CRT), and can further be used in connection with CRT-based analysis and/or correction. For instance, the detected BCG characteristic can be used in suppressing undesirable heart functions and/or in otherwise coordinating heart contractions. In connection with these embodiments, it has been discovered that BCG characteristics can be detected while pacemaker parameters are adjusted as part of CRT-based control, and used to identify desirable pacemaker parameters via corresponding BCG characteristics. For example, a statistically significant increase in maximum BCG amplitude can be obtained for various (e.g., six) subjects at desirable or optimal pacing settings, versus other/suboptimal settings ($p<0.05$).

In one implementation, a processor circuit of a BCG system as described above automatically sets cardiac resynchronization therapy (CRT) pace parameters for the user (e.g., as a maximum amplitude or minimum ECG R-wave to BCG J-wave interval) based on the output BCG signal. In some implementations, the BCG system further includes an implantable device having an accelerometer, and the processor circuit sets the CRT pace parameters based upon an output from the accelerometer. The accelerometer can be integrated within an implantable pacemaker, and coupled with lead-derived ECG, and can be used with one or more of the techniques discussed herein as a BCG analog for automatic self-adjustment (e.g., when the patient is standing on something somewhat compliant) to provide feedback regarding cardiac output to the pacemaker.

Other implementations are directed to using a BCG system as discussed above to generate a visual or other indication that can be used to set pacemaker parameters. The processor circuit generates an output BCG signal indicative of BCG signal variations due to changes in pacemaker parameters. For CRT, these parameters could include, for example, the interventricular pacing delays, or the atrio-ventricular pacing delays.

These CRT-based implementations are also amenable for open-loop or closed-loop adjustment of implantable pacemakers in a clinic setting. For example, a doctor can adjust the pacemaker settings with specific hemodynamic feedback. Such settings may involve, for example, adjusting a timing delay between pacing in different chambers to achieve a feature on a detected BCG signal corresponding to maximum cardiac output or maximum cardiac contractility. In certain applications, a wireless link is used for wireless communication between the implanted pacemaker and a scale (or other device) detecting BCG characteristics while a subject stands on the scale to provide for closed-loop pacing parameter adjustment.

While adjusting pacemaker settings, BCG measurements are monitored and used to detect ejection force and/or other heart-based characteristics. Using this approach, desirable pacemaker settings can be identified as those that result in a desirable ejection force. This monitoring and related settings can be carried out visually, such as by providing a visual signal indicative of a patient heart's ejection force, or automatically using a circuit or programmed computer to automatically generate a desirable setting in response to detected BCG characteristics.

In some implementations, the pacing pulses are used as triggers for ensemble averaging, triggered-averaging, or otherwise filtering measured BCG signals. With this approach, it has been discovered that a higher quality averaged or filtered BCG signal can be obtained than by using the timing of the ECG QRS complex itself. The pacing pulse timings can be extracted, for example, from the processor in the implantable device, the pacemaker programmer device in the clinic, or simply from pacing pulse artifacts in a simultaneously-measured surface ECG signal.

Another example embodiment is directed to a BCG system as described above, having a bodyweight sensing scale with an ECG and/or photoplethysmograph sensor integrated into the scale platform, detachable unit, or separate unit connected to the scale. In some implementations, the BCG capture device is integrated with the bodyweight sensing scale, and the secondary sensor is integrated with handlebar electrodes. The electrodes and secondary sensor detect at least one of an electrocardiogram (ECG) or photoplethysmography characteristic of the user. The processor circuit generates output BCG signals over time to provide an indication of at least one of cardiac output and stroke volume for determining a treatment need for the user, such as for titration of care for the user (e.g., for the adjustment of medicine dosage (with physician consultation) or signaling the need for a clinical visit).

In some implementations, the BCG capture device is integrated with the bodyweight sensing scale, and the secondary sensor is integrated in at least one of the scale platform, a detachable module, or a separate module connected to the scale via hardwire or wireless link. The secondary sensor detects a photoplethysmography characteristic of the user. The processor circuit generates output BCG signals over time to provide an indication of at least one of cardiac output and stroke volume for titration of care for the user.

In some implementations, changes in the BCG signal over time can be coupled with changes in bodyweight over time to assess a patient's overall health. For example, for heart failure patients, the fluid status indication derived from bodyweight changes can be supplemented by the cardiac output or stroke volume changes estimated by the BCG sensor to assess both congestion and perfusion of the patient. For instance, increasing body weight coupled with decreasing BCG RMS power could indicate worsening condition and the need for increasing diuretic dosage (with physician consultation) or a clinical visit.

Another example embodiment is directed to screening patients such as athletes to generate data from BCG signals. A processor circuit as described above is configured to generate an output BCG signal indicative of BCG RMS power to provide an indication of cardiac fitness. This approach can be used, for example, to characterize ventricular mass of a patient being screened to detect abnormalities or other heart-related conditions, in addition to and/or as an alternative to detecting other heart characteristics as described herein. In connection with these embodiments, it has been discovered that detected BCG characteristics can be indicative of left ventricular mass (LVM) of the patient being screened. A detected BCG signal is integrated, and a high or maximum value of the integrated signal is used as an indicator of momentum change. In many implementations, a patient's weight is also used in connection with a detected BCG signal to characterize LVM.

Figure 1A:
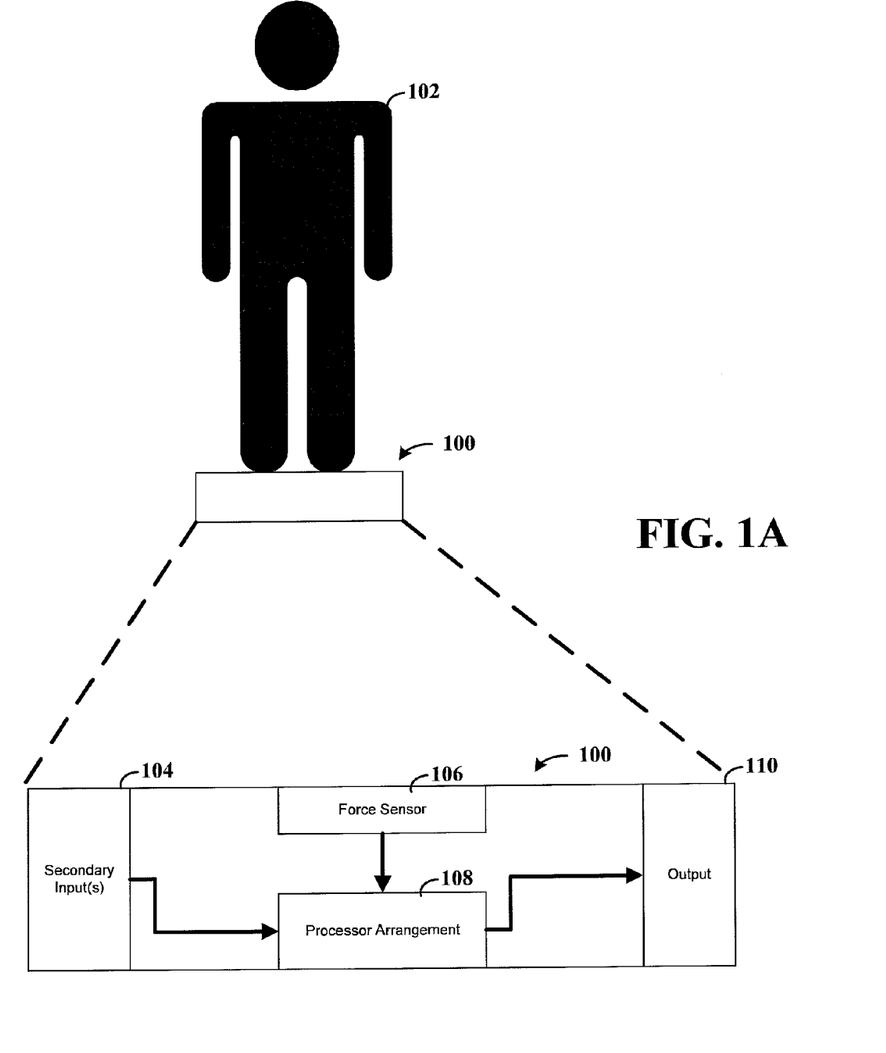
FIG. 1A shows a block diagram of a system and approach for determining cardiac function, consistent with an example embodiment of the present invention.
Figure 1B:
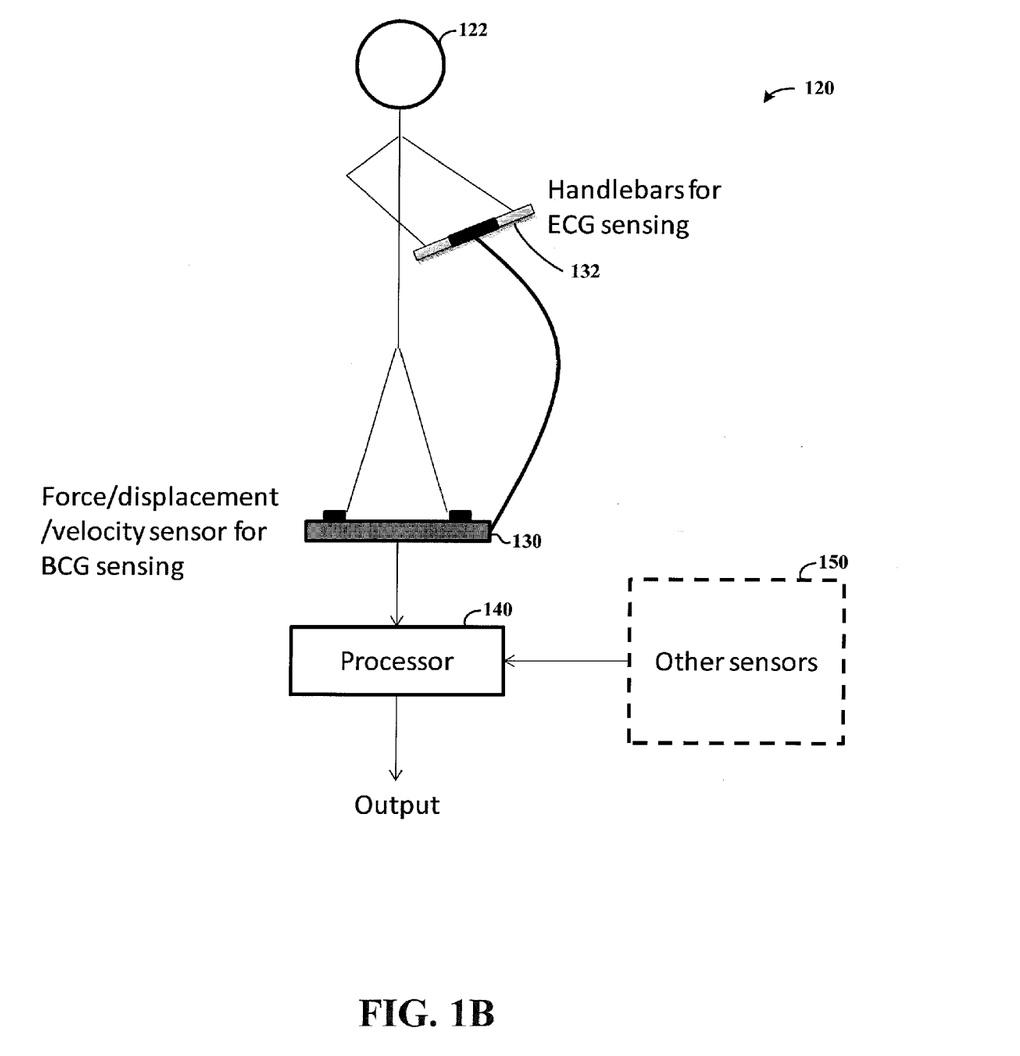
FIG. 1B shows a block diagram of a system and approach for detecting cardiac function, consistent with another example embodiment of the present invention.

In one implementation, a scale is modified for detecting BCG and single-lead ECG (e.g., as shown in FIG. 1B and described below). BCG and ECG signals are amplified by and interfaced to a computer for recording. The BCG beats for each subject are averaged using R-waves of the ECG as a trigger. In such implementations, a correlation between maximum magnitude of the BCG integral (MMBI) and LVM is significant (e.g., $R=0.68$, $p<0.01$), and the correlation between the product of MMBI and body weight, and LVM is stronger (e.g., $R=0.75$, $p<0.01$).

Other athletic characteristics, such as exercise recovery characteristics, can also be detected using these approaches. Measurement, processing, and analysis of all signals during exercise and/or recovery can be useful in evaluating an athletic condition. This evaluation can be particularly useful when compared to evaluating heart rate alone, as BCG characteristics as discussed herein can be correlated to work exerted by a user's heart per stroke, which can be used to evaluate exercise recovery in a manner that goes beyond the evaluation of a user's heart rate. For example, one implementation is directed to using a detected BCG characteristic to evaluate exercise recovery based on the time it takes for various parameters to return to their basal values or the maximum exertion achieved by the heart.

Turning now to the figures, FIG. 1A shows a block diagram of a system and approach for determining cardiac function/characteristics of a patient, consistent with an example embodiment of the present invention. User 102 positions themselves on scale 100. Scale 100 includes a force/weight sensor 106. This sensor 106 is configured to detect weight variations that are converted to an electrical signal that is sent to processing arrangement 108, and can be further used to provide the weight of the user, such as that provided by a traditional scale.

Secondary input(s) 104 provide information in addition to strict weight sensing. These inputs can include, for example, signals provided by heart-beat sensors, foot-to-foot impedance cardiogram sensors, user movement sensors and the like, which may further be incorporated into the system. In some implementations, impedance plethysmography or photo-plethysmography sensors, can be used to improve signal processing.

Still other implementations are directed to addressing motion artifacts, such as by using a secondary non-contact displacement sensor to measure correlated cardiac related information and uncorrelated body motion noise and remove motion artifacts. One such implementation involves using a displacement transducer such as an optical or acoustical emitter/detector sensor, to measure absolute or relative changes in body motion to improve the cardiac signal. Another approach to removing motion artifacts involves using multichannel sampling on individual strain gages (e.g., as described in connection with FIG. 2), or by switching a bridge circuit to capture different motion axes.

The processing arrangement 108 is configured to use the secondary input(s) 104 and various filtering algorithms to remove extraneous noise or interference on the signal from sensor 106. The results of this processing/filtering can be sent to an output 110, such as an LCD display or local memory. This information can be presented in a recordable form, such as for recording by the patient using the system, or for uploading for access by a doctor at a remote location. In some instances, the output 110 includes a network interface type device that provides an output to a network (e.g., Ethernet or wireless) connected to one or more storage devices that receive output data from scale 100. In other instances, the output 110 includes one or more of a Universal Serial Bus (USB) connection, removable memory card device, contactless card device, or a relatively simple indictor that indicates that abnormal cardiac function has been detected (e.g., warning the patient to contact a doctor).

According to one implementation, an ECG signal (single or multiple lead) is recorded simultaneously with weight-related detection (e.g., weight variations as discussed above) and used as a secondary input condition together with the detected weight-related condition. The signals from these recordings are combined using adaptive filtering, such as by adaptively filtering a secondary signal to determine the best least-squares estimate of the BCG signal from a raw weight measurement waveform. This approach leverages the fact that the ECG and BCG signals are correlated in time, while the noises in these waveforms are statistically independent.

In another implementation, heart rate (e.g., ECG or photoplethysmogram)-triggered ensemble averaging is used to enhance the quality and consistency of the BCG signal. Such a technique leverages off the ability to easily detect heart contraction using any of a number of different techniques. Detected heart contractions are then used to select relevant portions of the detected weight measurement to use in ensemble averaging. For example, ensemble averaging may be used in connection with detected noise to mitigate noise in the BCG signal.

In various implementations, an adaptive filtering approach using a least mean squares algorithm is used to remove noise from the BCG signal with the ECG signal as a reference. BCG signals are ensemble averaged using the ECG R-wave as the trigger. This ensemble averaging can be both static (one average for the entire data set) and dynamic (synchronous moving average). Additionally, respiration signal can be used as a reference for adaptive noise cancellation of respiration from the BCG. In certain applications, the system in FIG. 1A is configured for self-calibration to eliminate instrumentation resonance, to decouple mechanical filtering of the signal by the scale other device used to capture the BCG signal.

In another embodiment, force-balanced BCG is used to reduce or eliminate the need to mechanically dampen the device 100 supporting the user. This approach is applicable to other sensor-type arrangements, such as a sensor located in a prone-position scale, a chair, a bed or otherwise.

FIG. 1B shows a block diagram of a system 120 for detecting cardiac function involving both ECG and BCG detection, consistent with another example embodiment of the present invention. The system 120 can be used in a manner similar to that as described above in connection with FIG. 1A, and further with the above examples using both ECG and BCG, for detecting conditions of a user's heart. A scale-type BCG sensor device 130 includes an ECG-type hand-held sensor 132 that detects ECG characteristics that are used in connection with BCG characteristics detected at the scale-type device 130. An output from the BCG sensor device 130 is passed to a processor 140 that processes the output and detected ECG and BCG characteristics therein, to determine a heart-based condition of a user 122. In various implementations, one or more additional sensors, represented at block 150, are also coupled to the processor 140, which uses the inputs as part of the determination of the heart-based condition (e.g., such as a vibration sensor that is used to remove noise in one or both of a BCG- and ECG-based signals).

Figure 2:
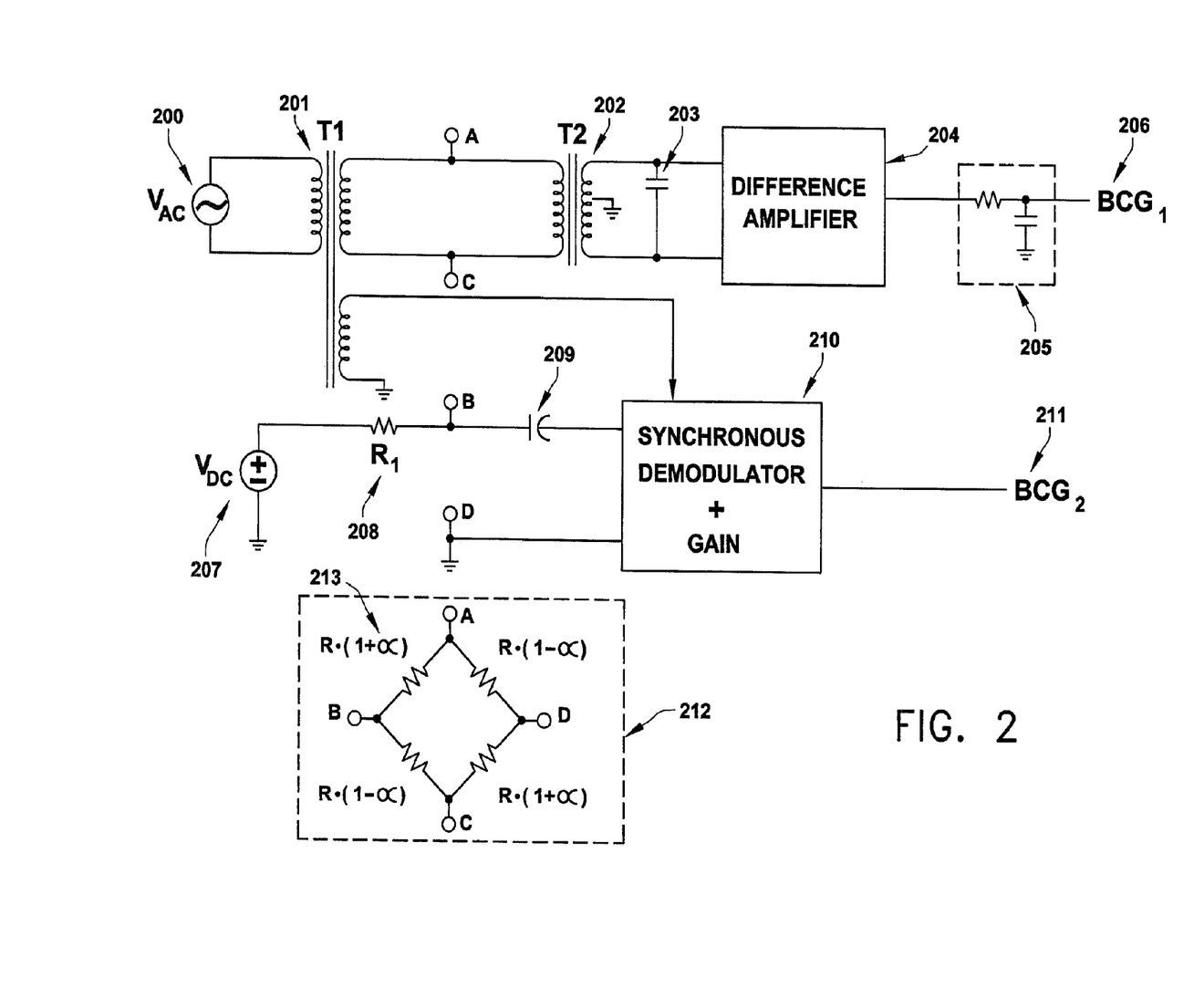
FIG. 2 shows a circuit diagram for simultaneously exciting the force sensor bridge in orthogonal configurations with two different frequencies, consistent with another example embodiment of the present invention.

In some applications, e.g., where the use of a secondary sensor may not be practical or is otherwise undesirable, a force sensor is arranged such that two force signals can be measured with correlated cardiac related information and incoherent motion noise. FIG. 2 shows an example embodiment amenable to implementation in such applications. A sine-wave voltage source 200 is configured to operate at a frequency that is higher than the frequency of the heart rate (e.g., 1 kHz), and is coupled to inputs A and C of a strain gauge circuit 212 via a first output winding of a transformer 201 (T1). The strain gauge circuit 212 is configured to vary the resistance of the bridge by a factor of alpha 213, which is proportional to the force imparted on the strain gauges.

The BCG signal, modulated by the frequency of the sine-wave source 200, appears across the terminals B and D and is AC-coupled by capacitor 209 into a synchronous demodulator and gain block 210. The second output winding of transformer 201 provides the synchronization signal to the demodulator and gain block 210. The output of 210 is the first BCG signal 211. A DC voltage 207 is input to resistor R1 208. This causes a BCG signal to appear across terminals A and C of the strain gauge circuit 212, which is passed through transformer 202 (T2) to a filtering capacitor 203 and a difference amplifier 204. Using the characteristics of the AC signal produced by the sine-wave source 200 (which is at a frequency much higher than the heart rate), an RC low-pass filter 205 is used to attenuate this sine-wave signal, leaving the second BCG signal output 206.

The specific circuit depicted by FIG. 2 is exemplary of a number of different implementations that can be used to provide similar functionality. As with other aspects of the present invention, the various functionalities can be implemented using combinations of general purpose computers configured by specialized software, programmable logic devices, discrete circuits/logic and combinations thereof.

In connection with various embodiments, acquired signals as described herein are used in deriving/monitoring various different types of information including, but not limited to, heart rate, the force of ejection of blood from heart (which can be correlated to cardiac output), time delay from electrical depolarization to mechanical contraction of the ventricles, relationship between electrical and mechanical activity in the heart (relating to excitation-contraction coupling), diagnosis of various diseases (including congestive heart failure, coarctation, aneurysm, etc.), predicting future cardiac health trends and/or non-invasive blood flow and pressure measurements.

Various aspects of the present invention are directed to use in a home or other location where it may not be practical to have a trained technician or physician available. In one implementation, simultaneous BCG and ECG recordings from a commercial bathroom scale or chair are used to facilitate home monitoring of cardiovascular health in a compact and inexpensive platform for reliable BCG acquisition. BCG measurements can be implemented for chronic management of congestive heart failure (CHF) patients at home. Various methods and devices discussed herein can be useful for tracking fluid loading by both body weight and relative cardiac output. For instance, an increased weight measurement and decreased BCG signal may be used as an indication of worsening heart failure.

Certain embodiments are directed to using blood flow measurements detected via ultrasound to calibrate BCG features for each person. This can be particularly useful as each person's BCG may be different due to different physiology. A blood flow waveform can be used from ultrasound to precisely determine transfer function relating vascular flow to BCG signal. This transfer function could then be inverted and applied to a received BCG signal.

Figure 3:
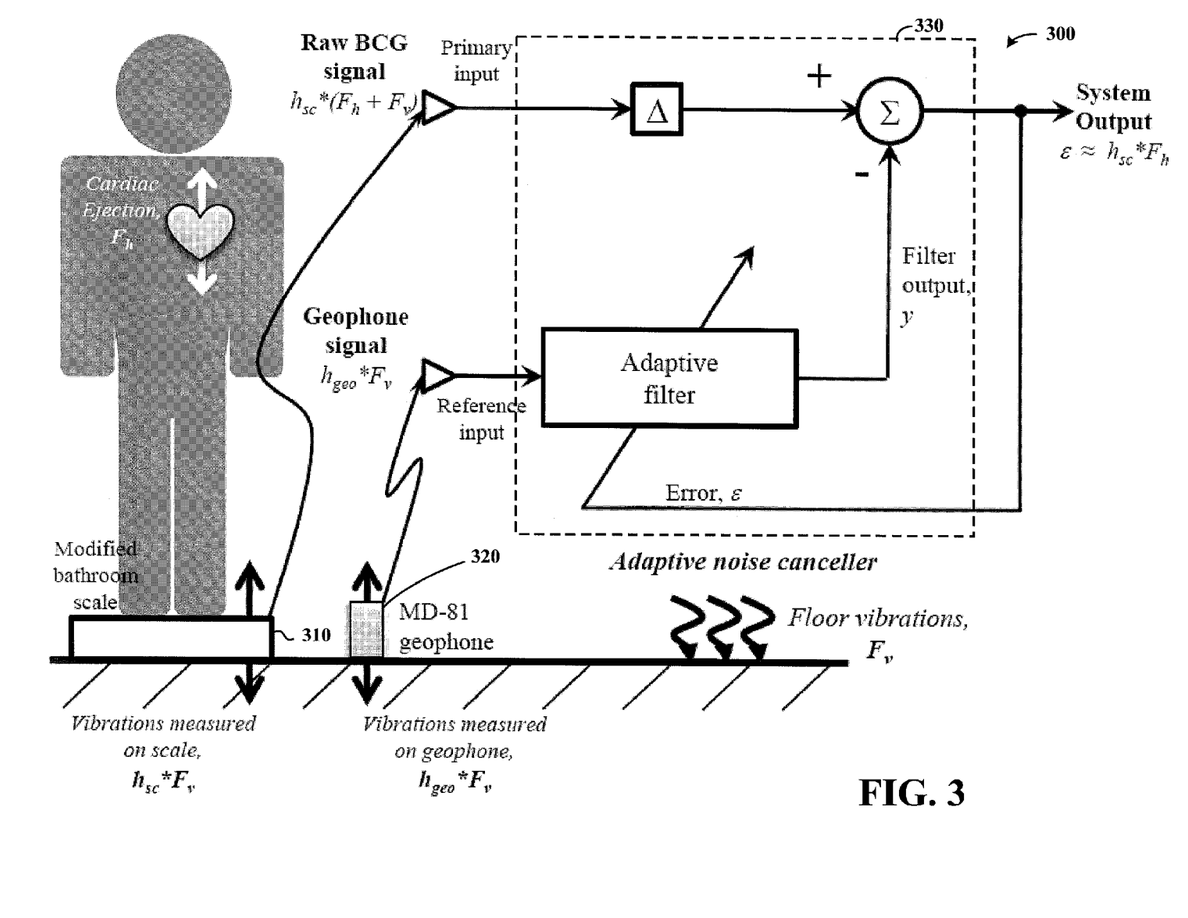
FIG. 3 shows a block diagram of a system and approach for detecting cardiac function and mitigating the effects of vibration in the local environment, according to another example embodiment of the present invention.

FIG. 3 shows a block diagram of a system and approach 300 for detecting cardiac function and mitigating the effects of vibration in the local environment, according to another example embodiment of the present invention. The system 300 includes a BCG sensor 310 having a scale-type sensor as discussed above, a vibration sensor 320 and an adaptive noise cancellation circuit 330. A BCG characteristic detected via the sensor BCG 310 is processed with a secondary characteristic detected at the vibration sensor 320, representing vibration present in surrounding structures. In some implementations, the sensor 320 may be placed to detect vibrations present in the BCG sensor 310 used to capture the BCG signal. As such, this secondary vibration is detected using a sensor that may be the same sensor as that used to detect the BCG characteristic, or a different sensor. By way of example, FIG. 3 shows a geophone sensor placed in close proximity to the BCG sensor/scale 310 used to detect BCG characteristics. The detected vibration is passed to the adaptive noise cancellation circuit 330 and used to process the BCG signal (also provided to the circuit 330). The system output from the adaptive noise cancellation circuit 330 thus includes a BCG analysis signal with mitigated (or removed) vibration-based noise. For example, interference can be reduced in measured weight signals that occur due to these vibrations (e.g., as part of an adaptive noise cancellation process).

Figure 4:
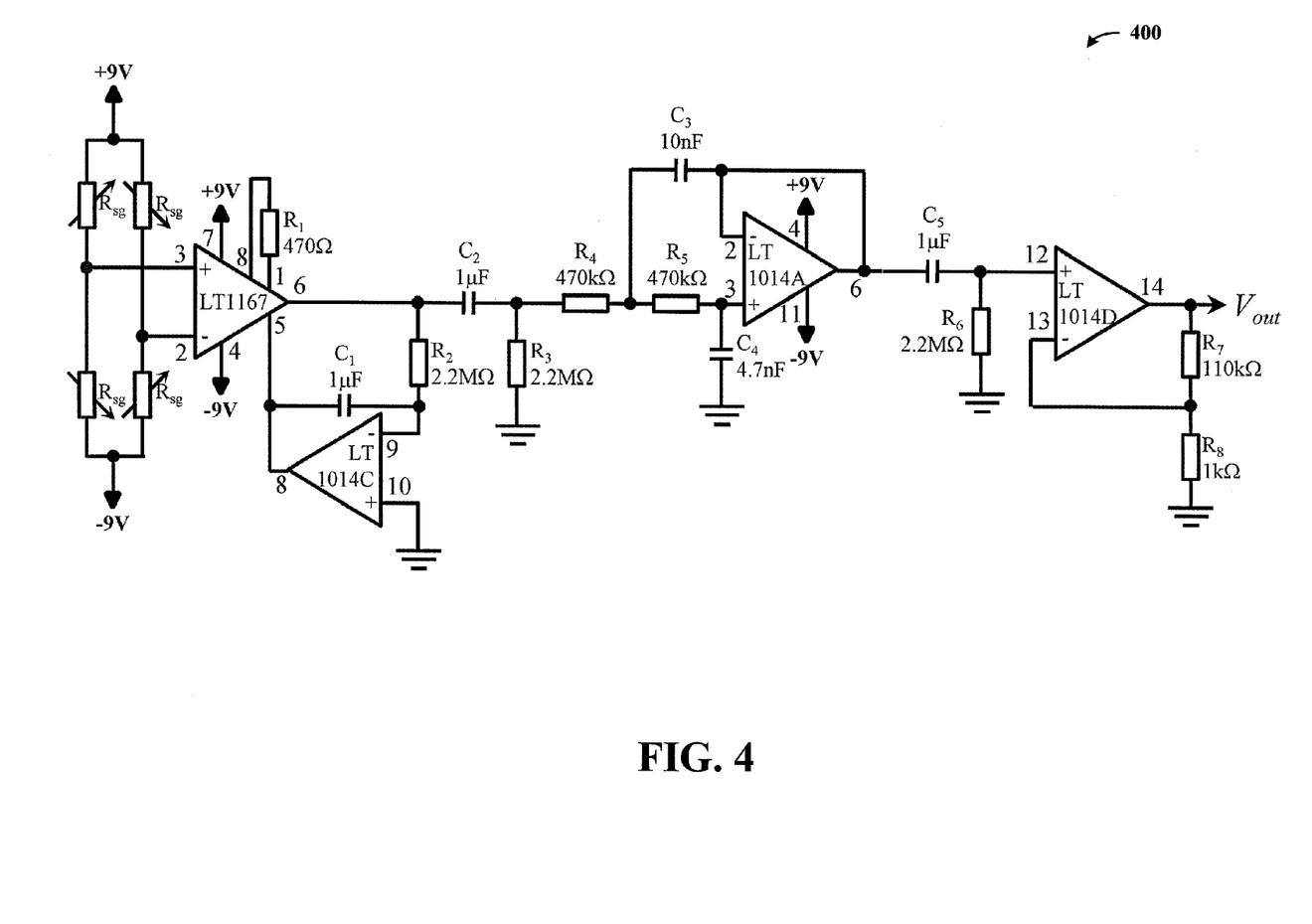
FIG. 4 shows a circuit for acquiring BCG signals from a commercial weighing scale, consistent with another example embodiment of the present invention.

FIG. 4 shows a circuit 400 for acquiring BCG signals from a commercial weighing scale, consistent with another example embodiment of the present invention. The circuit 400 is amenable to BCG acquisition from a weighing scale. The strain gauges within a commercial scale, such as an Omron HBF-500 scale, are arranged in a Wheatstone bridge configuration. The bridge is excited by a dc voltage of +/−9V, and the differential voltage across the bridge is amplified by an instrumentation amplifier (the LT1167) which is dc-blocked using integrative feedback (LT1014C). The output from this dc-blocked instrumentation amplifier stage is then band-pass filtered and further amplified. The circuit gain is 90 dB, with a bandwidth sufficient for high-resolution BCG acquisition.

The specific circuit depicted by FIG. 4 is exemplary of a number of different implementations that can be used to provide similar functionality. As with other aspects of the present invention, the various functionalities can be implemented using combinations of general purpose computers configured by specialized software, programmable logic devices, discrete circuits/logic and combinations thereof.

The following description references various Appendices submitted herewith, in connection with various example embodiments. Each of these Appendices is fully incorporated herein by reference.

Referring to Appendix A (Adaptive Cancellation of Floor Vibrations), aspects of the present invention are directed to adaptive cancellation of floor vibrations, as applicable to one or more of the following exemplary embodiments:

1. An auxiliary sensor, such as a geophone or accelerometer, is placed on the floor in close proximity to a BCG sensor, such that it detects the vibrations of the floor.
2. An adaptive noise canceller is configured, with a BCG signal as a primary input, and a secondary signal as a reference input, to generate a system output that includes a filtered BCG signal with the vibration artifacts removed.
3. An adaptive canceller circuit is trained or otherwise configured, before BCG measurements are taken from a person, by placing weights on a scale that is used to capture a BCG signal. Using this approach, a BCG component can be set to and any measured signal is representative of floor vibrations. The measured signal is thus used to identify floor vibrations and is used in subsequent analysis. In some implementations, filter coefficients are set based upon this measured vibration signal, and are used to achieve a best least squares solution. The coefficients can then be stored as initial conditions for an adaptive filter used in ensuing BCG measurements, which can facilitate real-time adaptive cancellation of floor vibrations without a long delay at the beginning of the recording for the system to converge.
4. BCG signals are captured from a number of subjects in a transport vehicle, clinic, or similar setting, using a single auxiliary sensor as a floor vibration noise reference for all BCG sensors. In one example involving a vehicle such as a bus, each seat is equipped with a BCG sensor and a single sensor (e.g., geophone or accelerometer) is placed on the floor, acting as a noise reference for all of the BCG measurements. Each BCG sensor uses an adaptive canceller, with an adaptive filter using a transfer function relating to the noise reference pick-up of floor vibrations to the pick-up of each individual BCG sensor.

Referring to Appendix B (IEEE EMBS 2009 Conference Paper), aspects of the present invention are directed to BCG signal estimation and to Cardiac Contractility Assessment Using BCG, as applicable to one or more of the following exemplary embodiments:

1. A BCG "pulse response" is defined as a BCG characteristic for each subject that may persist for a longer time period than a single heartbeat. This pulse response may, for example, include a mechanical response of the arteries and body to the pulse of blood ejected by the heart; these mechanical structures may continue oscillating long after this initial pulse of blood, causing the average BCG response to be longer in duration than a single heartbeat. In this context, the pulse response is used in characterizing aspects of the subject from which the BCG response is captured.
2. ECG R-wave timing is used as a timing reference to compute a "short-window" ensemble average BCG. This short-window average is then used to estimate the amplitude of each BCG heartbeat for the entire recording. BCG heartbeats are then re-segmented using an ECG timing reference with a "long-window" process. These long-window beats are then averaged after subtracting surrounding beats from each BCG heartbeat, yielding an interference-cancelled long-window BCG pulse response.
3. Damping of the mechanical afterwaves of a BCG pulse response are used to characterize arterial compliance (e.g., where less compliant arteries provide less damping and can be characterized as such).
4. The interval between the ECG R-wave and the BCG J-wave (R-J interval) is inversely correlated to changes in cardiac contractility. The R-J interval is used to characterize the contractility, in which a higher contractility leads to a lower R-J interval, and vice versa.
5. The signal-to-noise ratio (SNR) of each heartbeat is detected using normalized ensemble correlation and, in some implementations, R-J intervals are disregarded for heartbeats with relatively lower SNR.
6. The time interval between the pre-ejection period (PEP) and the R-J interval for each subject is used to characterize arterial compliance. Less compliant arteries are identified via shorter propagation delay between the ejection of blood at the heart and a mechanical wave detected at the feet of a subject (e.g., as akin to a rigid pipe propagating an acoustic wave faster than a compliant, soft pipe).

Referring to Appendix C (Foot EMG), aspects of the present invention are directed to using a foot-based EMG (Electromyogram) signal, as applicable to one or more of the following exemplary embodiments:

1. Electromyogram (EMG) measurements taken from the feet of a subject are used to detect (or flag) motion artifacts in the BCG signal of a standing subject. These artifacts are correspondingly used in processing or otherwise presenting a BCG signal.
2. EMG measurements are recorded from footpad electrodes (e.g., as used for bioimpedance-based body-fat measurements) of commercial weighing scales, and correspondingly used for generating a BCG signal as described herein.
3. The moving root-mean-square (RMS) power of the EMG signal, from the feet, is used to determine whether the motion of the subject is excessive. For instance, detecting a relatively higher RMS power of an EMG can be used as an indication of an increase in motion, and accordingly used in considering any measurements (e.g., to throw out or otherwise diminish the application of a particular signal).
4. Time delays between an EMG signal and BCG noise are corrected to correlate noise for effective noise detection.
5. The RMS power of the EMG during each heartbeat is used for generating a result using maximum likelihood weighted averaging algorithms, in which a weighted ensemble averaged BCG beat is computed by weighting each heartbeat in the ensemble average higher for lower RMS EMG power and lower for higher RMS EMG power.

Referring to Appendix D (Robust BCG Acquisition for Home Monitoring), aspects of the present invention are directed to BCG acquisition at home, as applicable to one or more of the following exemplary embodiments:

1. A BCG signal is used in conjunction with bodyweight measurements on a scale that is also used for monitoring the health of heart failure patients at home. The BCG signal is used to provide a measure of changes in perfusion by estimating changes in cardiac output; bodyweight measurements can (e.g., simultaneously) provide an estimate of congestion by evaluating weight change due to fluid retention. Both of these measurements can be combined to provide a desirable assessment of a person's cardiac health, since subjects can have congestion without perfusion or perfusion without congestion.
2. Photoplethysmograph and ECG signals are used for averaging or filtering a BCG signal, such as obtained herein.
3. Beat-by-beat BCG amplitude (J-wave) is used to characterize the stroke volume for a particular beat to which the wave applies.
4. The ECG R-wave timing is used as a timing reference to compute a "short-window" ensemble average BCG. This short-window average is then used to estimate the amplitude of each BCG heartbeat for the entire recording. BCG heartbeats are then re-segmented using the ECG timing reference, with a "long-window" process. These long-window beats are then averaged after subtracting surrounding beats from each BCG heartbeat, yielding an interference cancelled long-window BCG pulse response.

Referring to Appendix E (Non-invasive cardiac output trending using BCG), aspects of the present invention are directed to non-invasive detection of cardiac output, as applicable to one or more of the following exemplary embodiments:

1. Changes in the BCG RMS power are detected and correlated to changes in cardiac output.
2. A single measurement is taken using a gold standard clinical technique (e.g., Doppler ultrasound) to calibrate the RMS power of a subject to the subject's cardiac output. This baseline value is stored in (or accessible to) the device taking BCG measurements, and the baseline value is used to convert subsequent measurements to absolute measurements of cardiac output.
3. A circuit such as shown in FIG. 2 of Appendix E is used for BCG acquisition, in connection with various example embodiments.
4. BCG measurements are taken regularly over time and compared to a baseline measurement, such as discussed above, and used to identify therapeutic decisions such as diuretic dosage and others.
5. BCG measurements are taken before and after exercise, and features of the signal (such as RMS power) are compared to diagnose diseases and/or conditions. For example, a heart failure patient may not see an increase in RMS BCG power after exercise, whereas a healthy person certainly would; detecting RMS BCG power can be used to identify relative heart conditions.

Referring to Appendix F (Valsalva Paper), aspects of the present invention are directed to using a Valsalva maneuver, as applicable to one or more of the following exemplary embodiments:

1. BCG measurements are taken during a Valsalva maneuver to elicit various expected reflexes from the cardiovascular system. A response to the Valsalva maneuver can be used to diagnose diseases or conditions. For example, a patient with prior myocardial infarction may not see increased BCG amplitude after releasing the strain, whereas a healthy subject certainly does. BCG amplitude can thus be monitored and used to identify such conditions.
2. For cases when a simultaneous ECG is unavailable, a BCG J-wave rise time is used as an indication of changes in cardiac contractility.
3. A frequency domain analysis of a BCG signal is performed and used to provide indications of the state of cardiac contractility, by examining the ratio of high-frequency to low-frequency power in the power spectral density of the BCG.

Referring to Appendix G (Two Electrode Biosignal Amplifier for ECG Measurement), aspects of the present invention are directed to measuring an ECG, as applicable to one or more of the following exemplary embodiments:

1. An ECG is measured in "current-mode" using a transimpedance amplifier front-end, which leads to a low differential input impedance, and mitigates microphonic cable noise that can occur due to the movement of the cables during acquisition.
2. Current feedback is delivered to an input terminal using a non-inverting integrator sensing low-frequency variations in an output signal, and used to stabilize common-mode voltage at the input and prevent amplifier saturation and other undesirable, commonly-encountered problems in two-electrode (as opposed to typical three-electrode) ECG recordings.
3. A micro-power op-amp is used with the bandwidth boosted by a composite amplifier design, facilitating desirable current consumption (e.g., about 3.9 micro-Amps), such that a battery could operate the device continuously for years.
4. A lead-capacitor is used in the first stage of a composite amplifier to set a second-order sharper roll-off in the overall closed-loop response of the circuit, facilitating a greater degree of attenuation at the Nyquist frequency for sampling in analog-to-digital conversion of the signal.
5. A resistor is placed at a non-inverting terminal of an input op-amp, connecting this terminal to ground, matching the common-mode input impedances at the two input terminals. This approach can be used, for example, to facilitate an optimized (e.g., desirable) common-mode rejection ratio.
6. An ECG circuit is embedded in the handlebar electrodes of a commercial weighing scale to provide an R-wave timing reference for BCG signal averaging.
7. An ECG circuit is used for acquiring other biomedical signals, such as electroencephalogram (EEG) signals from the scalp.

The various embodiments described above are provided by way of illustration, and should not necessarily be construed to limit the invention. Based on the above discussion, those skilled in the art will readily recognize that various modifications and changes may be made to the present invention without strictly following the exemplary embodiments and applications illustrated and described herein. For example, algorithms, calibration, and verification methods developed for this system can be used for any BCG measurement system including beds and tables. Other scale configurations, such as a seated or prone configuration, can be used with the scale held vertically or at other relative angles. Custom strain gauges can be used in lieu of a scale interfaced to the similar electronics as discussed herein. Several alternative electronics configurations are used for various embodiments, some of which may include lock-in based circuits. Multiple scales can be used to mitigate or eliminate noise, such as by placing a scale under each leg of a chair-based circuit, and by constructing a larger bridge circuit. A number of exemplary and experimental implementations are discussed in detail in the appendices attached in the above-referenced provisional application, which are fully incorporated herein. The teachings of this disclosure include those teachings found in the appendices (A-G) for much of the above-noted discussion of example embodiments, and the various teachings can be implemented either alone or in combination with one another. The skilled artisan would appreciate the contemplated context of the teachings found in the appendices, e.g., in light of overlapping technical discussion. These and other modifications and changes do not depart from the true spirit and scope of the present invention.

What is claimed is:

1. An apparatus comprising:
    a weighing scale;
    a first user-physiological sensor including a heart-characteristic sensor configured and arranged to capture, from a user, a ballistocardiogram (BCG) signal for a plurality of a heartbeats from the user based on at least one of physical movement and mechanical output of the user's heart while the user stands at a stationary position on the weighing scale;
    a second user-physiological sensor configured and arranged to detect an indication of at least one of noise present in the BCG signal and a physiologic characteristic of the user, and to provide an output signal characterizing the detected indication;
    a processor circuit configured and arranged to process the BCG signal by filtering motion and noise from the BCG signal due to user movement, using the output signal as provided by the second user-physiological sensor, and by using the BCG signal, as filtered, to generate a cardiac-indicative signal indicative of a condition of the user's heart; and
    an interface circuit configured and arranged to track changes for a cardiac condition, or indicate an abnormal cardiac condition, relative to the user's physiologic characteristic using the cardiac-indicative signal from the processor circuit.

2. The apparatus of claim 1, wherein the second sensor is integrated in an external device that includes communication circuitry configured and arranged to communicate with the weighing scale.

3. The apparatus of claim 2, wherein the external device is a user-wearable circuit including circuitry configured and arranged to monitor physiological parameters of the user and the communication circuitry is configured and arranged to communicate at least one physiological parameter to the weighing scale.

4. The apparatus of claim 2, wherein the external device is a user-wearable circuit including circuitry configured and arranged to monitor physiological parameters of the user and output circuitry configured and arranged to communicate physiological parameters to the user.

5. The apparatus of claim 1, wherein the processor circuit is further configured and arranged to:
    access a cardiovascular waveform reference for the BCG signal, and
    estimate, using the cardiovascular waveform reference, a signal relative to noise present in the BCG signal and due to movement of the user while the user stands at a stationary position.

6. The apparatus of claim 1, wherein the generated cardiac-indicative signal includes an interference-cancelled BCG signal indicative of a condition of the user's heart and the processor circuit is further configured to generate the interference-cancelled BCG signal by using an input indicative of body movement or a hemodynamic parameter and by using a timing reference from the second sensor and a reference BCG signal to account for the noise interference.

7. The apparatus of claim 1, wherein the interface circuit configured and arranged to track changes for a cardiac condition, or indicate an abnormal cardiac condition includes tracking changes in the cardiac-indicative signal with changes in bodyweight of the user over time.

8. The apparatus of claim 1, wherein the interface circuit is further configured and arranged to indicate a heart condition in response to an increase in bodyweight of the user with a decrease in the cardiac-indicative signal over time.

9. The apparatus of claim 1, wherein
    the second user-physiological sensor includes an electrocardiogram (ECG) sensor configured and arranged to detect an ECG signal from the user, the detected ECG signal being indicative of a physiologic characteristic of the user, and to provide the output signal characterizing the physiologic characteristic to the processor circuit; and
    the processor circuit is configured with an algorithm for processing the BCG signal to generate the cardiac-indicative signal, or by using the detected ECG signal as an input to the algorithm or by filtering and averaging the BCG signal to generate the cardiac-indicative signal.

10. The apparatus of claim 1, wherein
    the second user-physiological sensor is configured and arranged to detect a physiological signal from the user and to provide the output signal characterizing the detected physiological signal, the physiological signal being at least one of an ECG signal and a photoplethysmography signal, and
    the processor circuit is configured to generate the cardiac-indicative signal by generating at least one of an ensemble-average and a triggered-moving average, of the detected BCG signal using the detected physiological signal.

11. The apparatus of claim 1, wherein
    the second user-physiological sensor includes an electrocardiogram (ECG) sensor configured and arranged to detect an ECG signal from the user and to provide the output signal characterizing the detected ECG signal, and
    the processor circuit is configured to use the output signal of the second user-physiological sensor to process the captured BCG signal by filtering and averaging the BCG signal to generate the cardiac-indicative signal.

12. The apparatus of claim 1, wherein
    the second user-physiological sensor includes an electrocardiogram (ECG) sensor configured and arranged to detect an ECG signal from the user and to provide the output signal characterizing the detected ECG signal, and
    the processor circuit is configured to generate the cardiac-indicative signal by generating at least one of an ensemble-average and a triggered-moving average of the captured BCG signal using the detected ECG signal, wherein said at least one of the ensemble-average and a triggered-moving average is used by the processor circuit to provide a waveform reference.

13. The apparatus of claim 1, wherein
    the second user-physiological sensor includes a photoplethysmography sensor configured and arranged to detect a photoplethysmography signal from the user and to provide the output signal characterizing the detected photoplethysmography signal, and the processor circuit is configured to generate the cardiac-indicative signal by generating an ensemble-average, or triggered moving average, of the detected BCG signal using the detected photoplethysmography signal.

14. The apparatus of claim 1, wherein the second user-physiological sensor includes a noise sensor configured to detect noise in the user's environment, including using a strain gage that is configured to detect noise by detecting user movement along a particular motion axis, and a heart characteristic sensor configured to detect a physiologic characteristic of the user's heart, and the processor circuit is configured to generate the cardiac-indicative signal by using the detected noise to mitigate noise in the captured BCG signal and using the detected heart characteristic to modify the captured BCG signal.

15. The apparatus of claim 1, wherein the processor circuit is configured to:

receive cardiac data indicative of at least one of cardiac output and stroke volume obtained from the user, and process the captured BCG signal by using the received cardiac data and both RMS power and an ensemble-average amplitude, to generate the cardiac-indicative signal indicative of the cardiac output of the user's heart.

16. The apparatus of claim 1, wherein the processor circuit is configured to compare the captured BCG signal to a baseline value, which is based upon cardiac output data for the user and both RMS power and an ensemble-average amplitude of the BCG signal, and to generate the cardiac-indicative signal indicative of the cardiac output and stroke volume of the user.

17. The apparatus of claim 1, where the second user-physiological sensor is an electrocardiogram (ECG) sensor configured and arranged to detect an ECG signal from the user and to provide the output signal characterizing the detected ECG signal, and the processor circuit and the interface circuit are configured to use pacing artifacts in the output signal from the ECG sensor to process the captured BCG signal by triggered averaging, ensemble averaging, or otherwise filtering the BCG signal.

18. The apparatus of claim 1, wherein the processor circuit and the interface circuit are configured to generate a signal to set cardiac resynchronization therapy (CRT) pace parameters for the user, using at least one of: a maximum amplitude; or minimum ECG R-wave to BCG J-wave interval of the output signal.

19. The apparatus of claim 1, wherein the processor circuit and the interface circuit are configured to generate the cardiac-indicative signal indicative of BCG signal variations due to changes in cardiac resynchronization therapy (CRT) parameters used by an implantable CRT device to regulate the user's heart, to provide an indication of cardiac responsiveness to CRT parameters.

20. The apparatus of claim 1, wherein the first user-physiological sensor includes a BCG capture device that is integrated with the weighing scale, the second user-physiological sensor is integrated with handlebar electrodes coupled to the scale, the electrodes and second user-physiological sensor being configured to detect at least one of an electrocardiogram (ECG) or photoplethysmography characteristic of the user, and the processor circuit and the interface circuit are configured to generate cardiac-indicative signals over time to provide an indication of at least one of cardiac output and stroke volume for determination of a treatment need for the user.

* * * * *